(12) United States Patent
Mitchell

(10) Patent No.: US 12,236,606 B2
(45) Date of Patent: Feb. 25, 2025

(54) SYSTEM AND METHOD OF EVALUATING NEURAL NETWORKS TO SEGMENT MEDICAL IMAGES

(71) Applicant: H. LEE MOFFITT CANCER CENTER AND RESEARCH INSTITUTE, INC., Tampa, FL (US)

(72) Inventor: Joseph Ross Mitchell, Tampa, FL (US)

(73) Assignee: H. LEE MOFFITT CANCER CENTER AND RESEARCH INSTITUTE, INC., Tampa, FL (US)

(*) Notice: Subject to any disclaimer, the term of this patent is extended or adjusted under 35 U.S.C. 154(b) by 376 days.

(21) Appl. No.: 17/613,642

(22) PCT Filed: May 26, 2020

(86) PCT No.: PCT/US2020/034537
§ 371 (c)(1),
(2) Date: Nov. 23, 2021

(87) PCT Pub. No.: WO2020/237242
PCT Pub. Date: Nov. 26, 2020

(65) Prior Publication Data
US 2022/0237785 A1 Jul. 28, 2022

Related U.S. Application Data

(60) Provisional application No. 62/851,975, filed on May 23, 2019.

(51) Int. Cl.
*G06T 7/11* (2017.01)
*G06T 7/00* (2017.01)
(Continued)

(52) U.S. Cl.
CPC .............. *G06T 7/11* (2017.01); *G06T 7/0012* (2013.01); *G06V 10/26* (2022.01); *G06V 10/82* (2022.01);
(Continued)

(58) Field of Classification Search
CPC ...................... G06T 7/11; G06T 7/0012; G06T 2207/10088; G06T 2207/20081;
(Continued)

(56) References Cited

U.S. PATENT DOCUMENTS

2013/0272587 A1* 10/2013 Fang ...................... H04N 19/60
382/128
2014/0341471 A1* 11/2014 Ono ...................... A61B 5/0042
382/173

(Continued)

OTHER PUBLICATIONS

International Search Report and Written Opinion in PCT/US2020/034537. Mailed Aug. 17, 2020. 8 pages.

(Continued)

*Primary Examiner* — John J Lee

(74) *Attorney, Agent, or Firm* — Meunier Carlin & Curfman LLC

(57) ABSTRACT

The first objective comparison of automated and human segmentation of magnetic resonance images, or MRI, using a blinded controlled assessment study. Computers connected over a network divide duties including computerized segmenting of the images, manual segmenting of the images, (Continued)

comparison of the computer segmented images and the manually segmented images, and scoring of the images for accuracy. The scores are evaluated to update configuration parameters of a neural network.

19 Claims, 10 Drawing Sheets

(51) Int. Cl.
    *G06V 10/26*     (2022.01)
    *G06V 10/82*     (2022.01)
    *G16H 30/20*     (2018.01)

(52) U.S. Cl.
    CPC ... *G16H 30/20* (2018.01); *G06T 2207/10088* (2013.01); *G06T 2207/20081* (2013.01); *G06T 2207/20084* (2013.01); *G06T 2207/30016* (2013.01); *G06T 2207/30096* (2013.01); *G06V 2201/03* (2022.01)

(58) Field of Classification Search
    CPC . G06T 2207/20084; G06T 2207/30016; G06T 2207/30096; G16H 30/20; G06V 10/82; G06V 10/26; G06V 2201/03
    See application file for complete search history.

(56) References Cited

U.S. PATENT DOCUMENTS

| | | | |
|---|---|---|---|
| 2016/0364876 A1 | 12/2016 | Guo et al. | |
| 2016/0364878 A1* | 12/2016 | Guo | G02B 27/0172 |
| 2017/0213067 A1* | 7/2017 | Padmanabhan | G06V 20/695 |

OTHER PUBLICATIONS

Wang et al. "A two-step convolutional neural network based computer-aided detection scheme for automatically segmenting adipose tissue volume depicting on CT images." In: Computer methods and programs in biomedicine. Mar. 21, 2017.

Alirezaie et al. "Neural network-based segmentation of magnetic resonance images of the brain." In: IEEE Transactions on Nuclear Science. May 1997.

* cited by examiner

SYSTEM AND METHOD OF EVALUATING NEURAL NETWORKS TO SEGMENT MEDICAL IMAGES

CROSS-REFERENCE TO RELATED APPLICATION

This application is a United States National Phase Patent Application of International Patent Application Number PCT/US2020/034537, filed on May 26, 2020, which claims priority to and the benefits under 35 U.S.C § 119 (e) of U.S. Provisional Patent Application Ser. No. 62/851,975 entitled "DeepBrain: Rapid Automatic Whole Brain Analysis from Neurological MRIs" filed May 23, 2019, both of which are hereby incorporated by reference herein in their entireties.

STATEMENT OF GOVERNMENT INTEREST

This invention was made with government support under Grant No. U01-CA220378 awarded by the National Institutes of Health/National Cancer Institute. The government has certain rights in the invention.

FIELD

This disclosure relates to systems and methods of training a neural network and evaluating its efficacy to segment magnetic resonance images (MRIs) for brain tumor identification, location and diagnosis.

BACKGROUND

Neural networks, often referred to as convolutional neural networks and deep convolutional neural networks, allow for applications of deep learning (DL) in medical imaging and have proliferated in the last few years. See, for example, "3D U-Net: Learning Dense Volumetric Segmentation from Sparse Annotation" (41). DL systems have proved particularly effective for segmenting organs and lesions in MRI and computed tomography ("CT") image volumes. By their nature, DL systems tend to be "black boxes," unable to provide insight into how their segmentation results were obtained. Consequently, a lingering issue is reproduction and validation of the many compelling results.

One kind of a deep learning system that has been used in non-limiting example embodiments herein, is referred to as DeepMedic. The developers of DeepMedic describe it as open source "software for brain lesion segmentation based on a multi-scale 3D Deep Convolutional Neural Network coupled with a 3D fully connected Conditional Random Field." See, e.g., website addresses at https://biomedia.doc.ic.ac.uk/software/deepmedic/ and https://github.com/deepmedic/deepmedic, promulgated by the Biomedical Image Analysis Group, Department of Computing, Imperial College London, London SW7 2AZ, UK.

Evaluation of DL-based segmentation with tools such as DeepMedic has focused primarily on measuring overlap with reference segmentations. Typically, the reference segmentations are created by radiologists or by expert technicians with training in image-processing. Often, these segmentations are then reviewed for accuracy by one or more independent radiologists. In essence, this process "front-loads" human expertise to improve the training and assessment of DL systems.

Even with open source tools for computerized segmentation, however, a need still exists in the industry for a complementary approach to the front loaded experiments described above—one that "back-loads" human expertise to evaluate (and potentially improve) the results of DL segmentation.

BRIEF SUMMARY

In one embodiment of this disclosure, a computer implemented method of determining accuracy of a neural network in producing computerized segmentations within magnetic resonant (MR) images includes steps of saving computer segmented images on a first computer connected to a network; communicating with test computers connected to the network, wherein the test computers display the computer segmented images alongside manually segmented test images for scoring; and receiving, at the first computer, scores for the accuracy of the manually segmented test images and the computer segmented images from the test computer.

In another embodiment, a computer implemented system of determining accuracy of a neural network in producing computerized segmentations within magnetic resonant (MR) images includes a segmenting computer having a processor connected to computerized memory storing software implementing the neural network, the computerized memory storing adjustable settings for neural network configuration parameters, wherein the segmenting computer receives the MR images as inputs to the neural network and segments regions within the MR images with the neural network to produce computer segmented images. A first computer connected over the network to the segmenting computer, wherein the first computer saves the computer segmented images. The first computer communicates with test computers connected to the network, wherein the test computers display the computer segmented images alongside manually segmented test images for scoring. The first computer receives the scores from the test computers for the accuracy of the manually segmented test images and the computer segmented images. Using the segmenting computer, technicians or automated software may update the neural network configuration parameters after receiving the scores.

BRIEF DESCRIPTION OF THE DRAWINGS

The skilled person in the art will understand that the drawings, described below, are for illustration purposes only.

DETAILED DESCRIPTION

Figure 1:
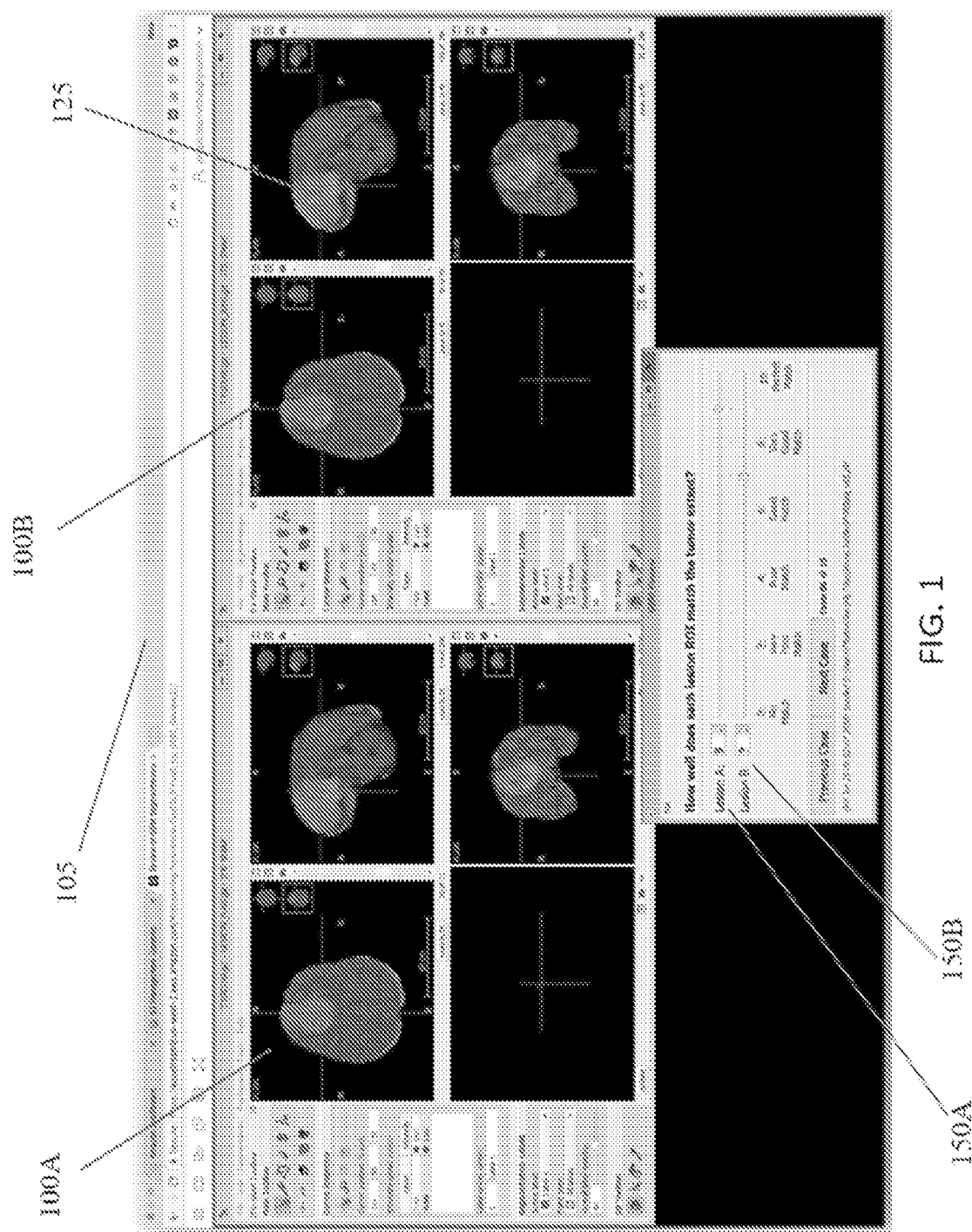
FIG. 1 shows one example display utilizing brain tumor segmentation review software, running on Amazon Web Services ("AWS") AppStream 2.0. AppStream allows the developer to run Windows in a virtual machine on AWS, and display the output to a remote instance of Google Chrome.

In some aspects, the disclosed technology relates to impedance-based quantification and microfluidic control. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. In terms of notation, "[n]" corresponds to the nth reference in the list. For example, [1] refers to the first reference in the list, Clarke L P, Velthuizen R P, Camacho M A, et al. MRI segmentation: methods and applications. Magn. Reson. Imaging. Elsevier; 1995; 13(3):343-68 https://www.ncbi.nlm.nih.gov/pubmed/7791545.

This study compiled a multi-institutional database of 741 pretreatment MRI exams. Each contained a post-contrast T1-weighted exam, a T2-weighted FLAIR exam, and at least one technician-derived tumor segmentation. The database included 729 unique patients (470 male, 259 female). Of these exams, 641 were used for training the DL system, and 100 were reserved for testing.

In general, this study developed a platform to enable qualitative, blinded, controlled assessment of lesion segmentations made by technicians and by a deep learning ("DL") neural network method. On this platform, twenty neuroradiologists performed 400 side-by-side comparisons of segmentations on 100 test cases by comparing the technician segmented images with computer segmented images. They scored each between 0 (poor) and 10 (perfect). Agreement between segmentations from technicians and the DL method was also evaluated quantitatively using the Dice coefficient, which produces values between 0 (no overlap) and 1 (perfect overlap).

In one non-limiting embodiment, results showed that the neuroradiologists gave technician and DL segmentations mean scores of 6.97 and 7.31, respectively (p<0.00007). The DL method achieved a mean Dice coefficient of 0.87 on the test cases.

In one embodiment, this was the first objective comparison of automated and human segmentation using a blinded controlled assessment study. The deep learning ("DL") system of this disclosure learned to outperform its "human teachers," and produced output that was better, on average, than its training data.

The disclosed system allows comprehensive and objective comparisons of DL and human segmentations via blinded controlled assessment studies. Multiple experts, potentially located across widely separated geographic regions, can easily access a cloud-based system, via a common, secure web browser.

This disclosure compares technician derived and DL derived segmentations of brain tumors. Often these are heterogeneous, diffuse, and highly infiltrative aggressive tumors. Consequently, it is a time-consuming task to segment brain tumors in MRI scans. Therefore, considerable effort has been devoted over the last 25 years to develop computer-based methods to accelerate and automate brain tumor segmentation (1-8). Recently, effort has focused on designing and training DL systems to segment these complex lesions (9-16). Careful validation of these systems is required to ensure translation to clinical workflows.

This study was reviewed and approved by the Mayo Clinic Institutional Review Board. Over the last 15 years researchers have been collecting and segmenting routine clinical MRI exams of brain tumor patients. This collection supports ongoing research into mathematical modeling of brain tumor growth (17). For example, in one embodiment, this study utilized a brain tumor database that contains 70,542 MRI studies (imaging time points) from 2,892 unique patients. These studies range in date from 1986 through 2019, and were acquired on both 1.5 T and 3.0 T MRI systems. An image analysis team, currently numbering 15 technicians, has segmented brain tumors in 38,535 of these time points.

Image analysts undergo a training program to ensure consistent performance. The underlying principle of the training is to learn, internalize, and apply complex rule sets across all magnetic resonance ("MR") modalities. Each rule set is based upon selecting the bright signal due to tumor presence as opposed to bright signal due to normal or abnormal non-tumor brain tissues. Each of these segmentations has been reviewed for accuracy by a segmentation supervisor prior to inclusion in the database. The supervisor has extensive experience segmenting brain tumors, but is not a board-certified neuroradiologist. However, a neuroradiologist is available for consult.

For this proof-of-concept experiment, some embodiments of this disclosure restricted the analysis to pre-treatment MRI studies, since treatment may cause significant alterations to brain appearance. That, in turn, may cause ambiguities in the manual segmentations which could impact the segmentation evaluation study. The above referenced database was searched to identify pre-treatment studies that included both a T1 post-contrast (T1c) scan along with a fluid-attenuated inversion recovery (FLAIR) scan. Both the T1c and FLAIR scans also had to have at least one segmented region each. This disclosure identified 914 pretreatment MRI studies from a brain tumor database. Of these, 741 met these inclusion criteria.

Some scans had multiple segmentations, each performed by a different technician. When two segmentations were available for a given scan researchers used the intersection of the two regions. When more than two segmentations were available these were combined into a consensus segmentation using majority voting, per-voxel. Each tumor was segmented into two compartments: enhancing signal on T1c, and bright signal on FLAIR. However, the use of two segmentation compartments greatly increased the cognitive burden during the visual assessment study (described below). Therefore, the two regions were combined into a single whole-tumor region using the union of the two compartments via a logical 'OR' operation, per voxel.

Preprocessing:

Each included study was processed using the following fully automated pipeline: 1) the MRI volumes and brain tumor segmentation files were copied from the database; 2) the extracted data was verified to ensure completeness; 3) the FLAIR volume was rigidly co-registered to the T1c volume using the SimpleElastix framework (18); 4) each volume was resampled to a common voxel spacing of 1×1×2 mm (x, y, z). This disclosure compared trilinear and tri-cubic interpolation for resampling. There was little visible difference between the two methods, likely because the target voxel size was smaller than the source voxel size, for the majority of exams. Therefore, this study selected trilinear interpolation; 5) contrast-to-noise ratio was improved using nonlinear curvature-flow noise reduction (19); 6) radio-frequency non-uniformity was reduced using the N4 algorithm (20); 7) the brain was masked within the head ("skull-stripped") using the MoNSTR algorithm (21); 8) the MR intensities of brain voxels were adjusted to have zero mean and unit variance; 9) the T1c and FLAIR segmented regions were combined using a per-voxel logical OR operation to create a binary mask representing the combined tumor region; and 10) the Harvard-Oxford probabilistic atlas (22) was nonlinearly transformed to fit the subject's brain.

The atlas was composed of two components: cortical and subcortical regions. Embodiments of this disclosure used the 1 mm isotropic voxels, maximum probability version in the experiments disclosed herein. Atlas alignment was accomplished using the SimpleElastix framework, following a procedure described previously (23). Briefly, it involves two steps: an initial affine transformation to coarsely align the ICBM152 template (24) to the subject brain; followed by a non-linear local b-spline transformation to refine the alignment. Since the Harvard-Oxford atlas is itself aligned with the ICBM152 template, the composite transformation used to align the template with the subject's brain may be used to align the atlas with the subject's brain. This process is known to have limitations, especially when significant alterations or pathology are present in a subject's brain (25). Consequently, one non-limiting intent was to use the aligned atlas as an aid for visualization.

In one example embodiment, a training set was used to train the open-source 3D "DeepMedic" convolutional neural network, described elsewhere (9). This network has achieved state-of-the-art results in the international Multi-modal Brain Tumor Segmentation (BraTS) challenges (10).

Network training is controlled via a large number of configurable parameters. Unless otherwise noted below, this disclosure used default parameter values described in detail in the software documentation. These parameters have been pre-tuned for brain tumor segmentation.

The 741 included exams were randomly divided into 600 training exams, 41 validation exams, and 100 test exams. During an initial hyperparameter tuning phase the 600 training exams and 41 validation exams were used to optimize two training hyperparameters: 1) the number of training epochs; and, 2) the learning rate step decay schedule. No other training hyperparameters were tuned during this process. In particular, the number of sub-epochs per epoch was fixed at 20, the initial learning rate was fixed at 0.001, and the step decay factor fixed at 2.0. Intensity augmentation was performed on the normalized MRI exams by adding to each voxel an intensity value randomly selected from a distribution with mean 0 and standard deviation of 0.1. No other data augmentation was performed.

The learning rate was halved at epochs 20, 30, 35, 40, and 45. Performance (mean whole tumor Dice coefficient (26), described below) on the validation data set plateaued after 50 epochs. Consequently, at epoch 50 researchers involved in this disclosure performed a stochastic gradient descent warm restart (27) (SGDR). Briefly, this operation has been shown to improve the performance of deep neural nets, especially when the parameter space may include multiple distinct near-optimal minima. This technique was selected as researchers suspected this may have been the case with the subject dataset due to its extensive variability. SGDR was accomplished by setting the learning rate back to 0.001, and continuing optimization for a further 24 epochs. During this period, the learning rate was halved at each of the following epochs: 59, 62, 65, 68, and 71.

Training was conducted on Amazon Web Services (AWS, Seattle WA) using an Amazon Machine Instance (AMI) customized for deep learning by Nvidia Inc. (Santa Clara CA). The AMI ran on an AWS p3.2x large instance equipped with an Nvidia Tesla V100 GPU, 8 Intel Xeon processors, and 64 GB of RAM. All training data was anonymized prior to being uploaded to Amazon Elastic Block Storage, where it was available to the p3 instance for processing.

Once the hyperparameter tuning phase was complete, training of an ensemble of five (5) networks for brain tumor segmentation began. Each instance of the DeepMedic network was initialized with random weights, then trained from scratch. The training process described above was followed, except the validation exams were included in the training dataset. Thus, the number of training exams was increased to 641. No validation set was used during ensemble training. The 100 test exams remained sequestered during this process.

Training required an average of 28 hours and 51 minutes per ensemble instance. A total of 144 hours and 15 minutes of execution time were required to train the entire ensemble of 5 networks. Multiple AWS virtual machines were used in parallel to reduce the elapsed training time. Once trained, each instance in the ensemble required an average of 791 seconds to segment the brain tumors in all 100 test exams (7.91 seconds/exam). A total of 3,953 seconds were required for all 5 ensemble instances to segment all 100 test exams (39.53 seconds/exam). In theory, 5 AWS virtual machines could be used in parallel, one per ensemble instance, to reduce the elapsed segmentation time per exam to approximately 8 seconds.

Agreement between the technician and DL segmentations was evaluated using the Dice coefficient(26). This value varies between 0 and 1 and indicates the degree of overlap between the 3D lesion segmentations. A value of 0 indicates no overlap, while a value of 1 indicates perfect overlap. The Dice coefficient was determined for each of the 100 test cases.

Neuroradiologist Review:

A review of the 100 test cases was performed by 20 board-certified neuroradiologists (1) from Moffitt Cancer Center and 19 from Mayo Clinic including: Rochester MN (12); Phoenix AZ (6); and Jacksonville FL (1)). The radiologists' number of years of work experience, post-certification in neuroradiology, ranged from 1 to 23 years with a mean (±standard deviation) of 14.2 (±8.0) years. The radiologists were asked to compare the technician and DL segmentations by viewing them side-by-side, then scoring each on a scale of 0 through 10 (FIG. 1). The radiologists were instructed to assign scores based on how well each segmentation matched the tumor extent visible in the MRI exam. They were informed that a score of 0 indicated that the segmentation had no overlap with the MRI visible tumor, while a score of 10 indicated that the segmentation perfectly matched the MRI visible tumor. The slider widgets used for specifying scores allowed the radiologists to specify integer values between 0 and 10. The sliders were enumerated as follows: 0: No Match, 2: Very Poor Match, 4: Poor Match, 6: Good Match, 8: Very Good Match, 10: Perfect Match.

The order of the displayed exams was randomized, and the radiologists were blinded to the source of the segmentation. Due to the workload involved, each radiologist was asked to perform 20 side-by-side comparisons. Therefore, the 100 test exams were randomly split into 5 groups, each containing 20 of the test exams. Each radiologist was randomly assigned to one of the 5 groups. Thus, each group of 20 test exams was examined by 4 independent radiologists (20 radiologists divided by 5 groups). In total, 400 side-by-side comparisons and evaluations were performed (20 radiologists times 20 exams per radiologist).

The review was performed using a custom-developed program running on the AWS AppStream 2.0 application streaming service. AppStream supports programs that can execute on Microsoft Windows Server 2012 R2 (Microsoft Inc., Redmond Wa.). The Windows operating system runs on a virtual machine. User input to, and graphical output from, this virtual machine is streamed over a secure https connection to/from an instance of the Google Chrome web browser (Google Inc., Mountainview Ca.) running on a remote device. This service allows the developer to select from a range of virtual machines with varying hardware capabilities. Some embodiments herein used the "stream.graphics-design.large" virtual machine instance in this experiment.

The radiologists used a high quality display with at least 1920×1080 pixels to perform the review. This work also included easily accessible documentation for the radiologists about the disclosed experiments and the segmentation review application on the virtual machine.

The 100 test exams and their associated manual technician and automatic DL segmentations were uploaded to 100 separate folders inside the AppStream virtual machine. Each exam folder contained 4 files: the T1c and FLAIR MRI volumes, and the technician and DL segmentations. All files were stored in NIfTI format. The segmentations in each folder were assigned a generic name, either "A" or "B", since this name was visible in the review application (below). The order of "A" and "B" was randomized between the technician and DL segmentations for each test exam.

The segmentation review application was written in Python 3.6, and used the QT v5 framework for its graphical interface (FIG. 1). The application displayed a window that allowed radiologists to step through the test exams in their assigned group, one at a time, forward or backward. The window also included widgets to allow the radiologists to easily enter and save segmentation scores.

The Python application launched two instances of ITK-SNAP(28) (http://www.itksnap.org) to display each test exam and the segmentations. Each ITK-SNAP instance loaded both the T1c and FLAIR volumes. The ITK-SNAP instance displaying segmentation "A" was positioned in the top left of the display, while the ITK-SNAP instance displaying segmentation "B" was positioned in the top right. The Python program invoked the Windows application "AutoHotKey" (https://www.autohotkey.com/) to arrange the ITK-SNAP and scoring windows on the display. When the radiologist chose to display the next (or previous) exam in their group, the Python program terminated the two ITK-SNAP processes, then repeated the process described above for the next (or previous) exam in the assigned group.

ITK-SNAP provided axial, sagittal and coronal views of the MRI volumes and segmentations. The segmentations were displayed as translucent overlays on top of the MRI volumes. The radiologists could change this transparency, alter the intensity contrast settings for either displayed MRI volume, and position the cursor and view anywhere within either MRI volume. The two ITK-SNAP instances were "synced" so that cursor position and display remained the same in both instances at all times showing the exact same 2D MRI slices.

Radiologists could complete their reviews over multiple sessions—all program state and scoring information were preserved between sessions. After a radiologist completed his or her group of 20 reviews, a single binary, machinereadable, file containing all their scores was retrieved from their AppStream account for analysis.

Results:

This study included 741 exams from 729 unique patients. The 741 exams had the following sex distribution: 451 male; 262 female; and, 28 sex not specified. The mean (±standard deviation) age of the patients was 53.5 (±16) years (Table 1). The cohort included: 525 MRI exams from 8 North American institutions; 185 exams from three public domain data sets; and, 12 exams from a consortium (Table 1). Included MRI exams ranged in date from 1990 to 2016, with a median acquisition year of 2006. The cohort contained 19 different tumor types (Table 2). The most common tumor type was Glioblastoma (449 of 741 exams, or 61%). One hundred and forty-five exams (20%) had a tumor type that was not specified.

Table 1 shows primary sources for the exams processed in this study. In total, 12 different North American academic cancer centers, 2 public domain datasets, and 2 foundation sponsored studies contributed exams. 'Study Source' indicates the origin of the MRI exams. 'N' indicates the number of exams contributed. 'Age' is the mean age (±standard deviation) of the patients when the exam was obtained. 'M/F (Not Specified)' indicates the number of male (M) and female (F) patients in the group. The number of patients whose sex was not specified is indicated in brackets. 'Study Dates' lists the range of years the exams were acquired, with the median year indicated in brackets. The last row provides summary values for the entire cohort. Credit: *Ivy Glioblastoma Atlas Project

TABLE 1

Primary sources for the exams processed in this study

| | Study Source | N | Age | M/F (Not Specified) | Study Dates |
|---|---|---|---|---|---|
| 1 | Cancer Centers (n = 8) | 525 | 53.1 ± 15.9 | 338/187 | 2000-2016 (2008) |
| 2 | TCGA-GBM | 101 | 58.4 ± 14.4 | 63/38 | 1996-2008 (2001) |
| 3 | TCIA | 85 | 45.6 ± 15.6 | 33/24 (28) | 1990-2005 (1994) |
| 4 | Ivy GAP* | 18 | 56.7 ± 13.4 | 7/11 | 1996-2000 (1997) |
| 5 | Radiation Therapy Oncology Group | 12 | 66.9 ± 17.0 | 10/2 | 2009-2011 (2010) |
| | Overall | 741 | 53.5 ± 16.0 | 451/262 (28) | 1990-2016 (2006) |

This dataset included: 1,482 3D MRI volumes (2 per study); 75,045 2D MR images (mean: 101 images per study, or 50 2D images per 3D MRI volume); and, 2,337 technician-generated 3D tumor segmentations (mean: 3.2 segmentations per study, or 1.6 segmentations per MRI volume).

Figure 2A:
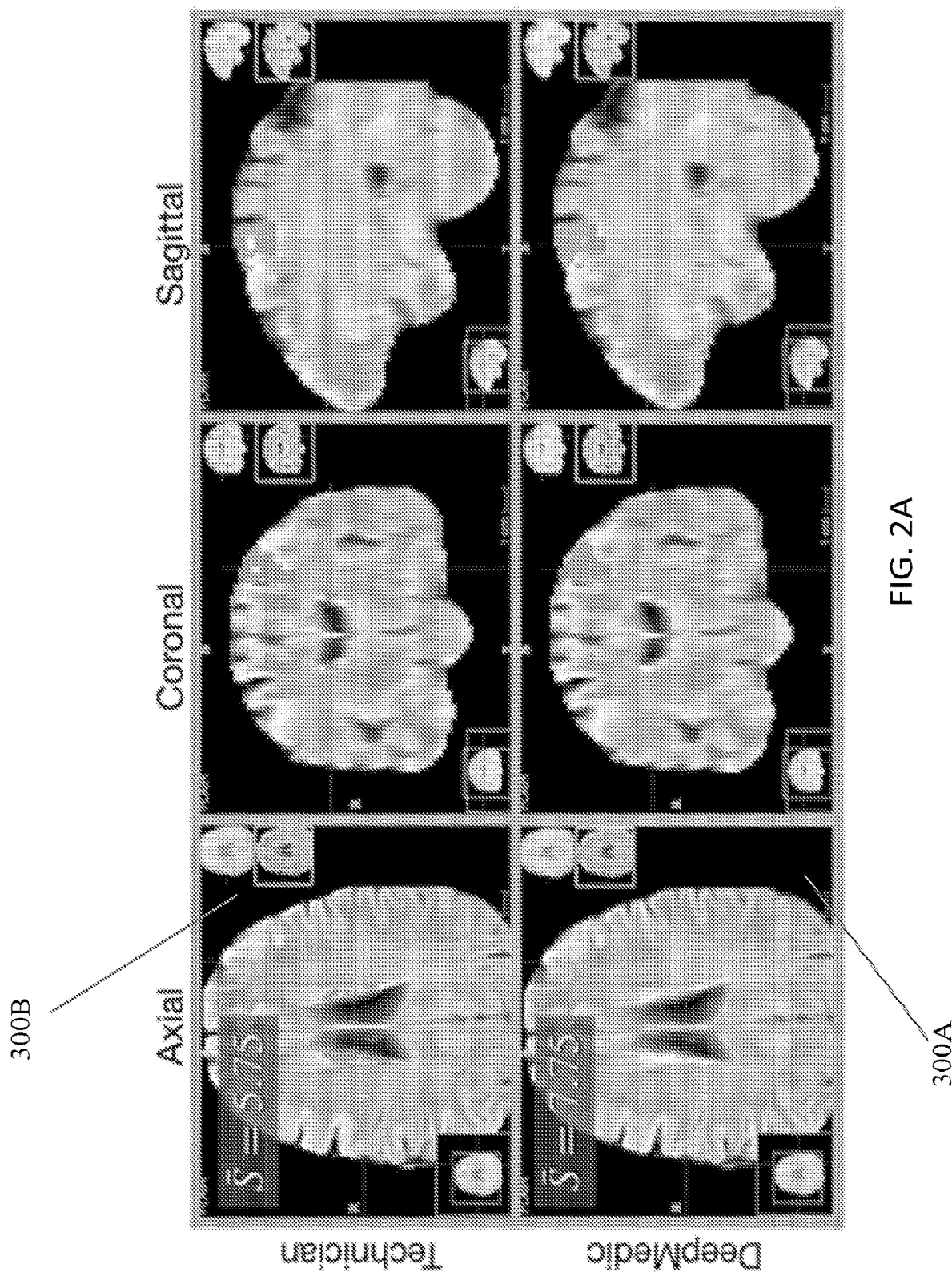
FIG. 2A shows a first set of images (Exam A with Dice=0.57) (FLAIR) from two test exams with the lowest Dice coefficients (poorest agreement between the technician and DeepMedic defined tumor regions) among the 100 test exams.
Figure 2B:
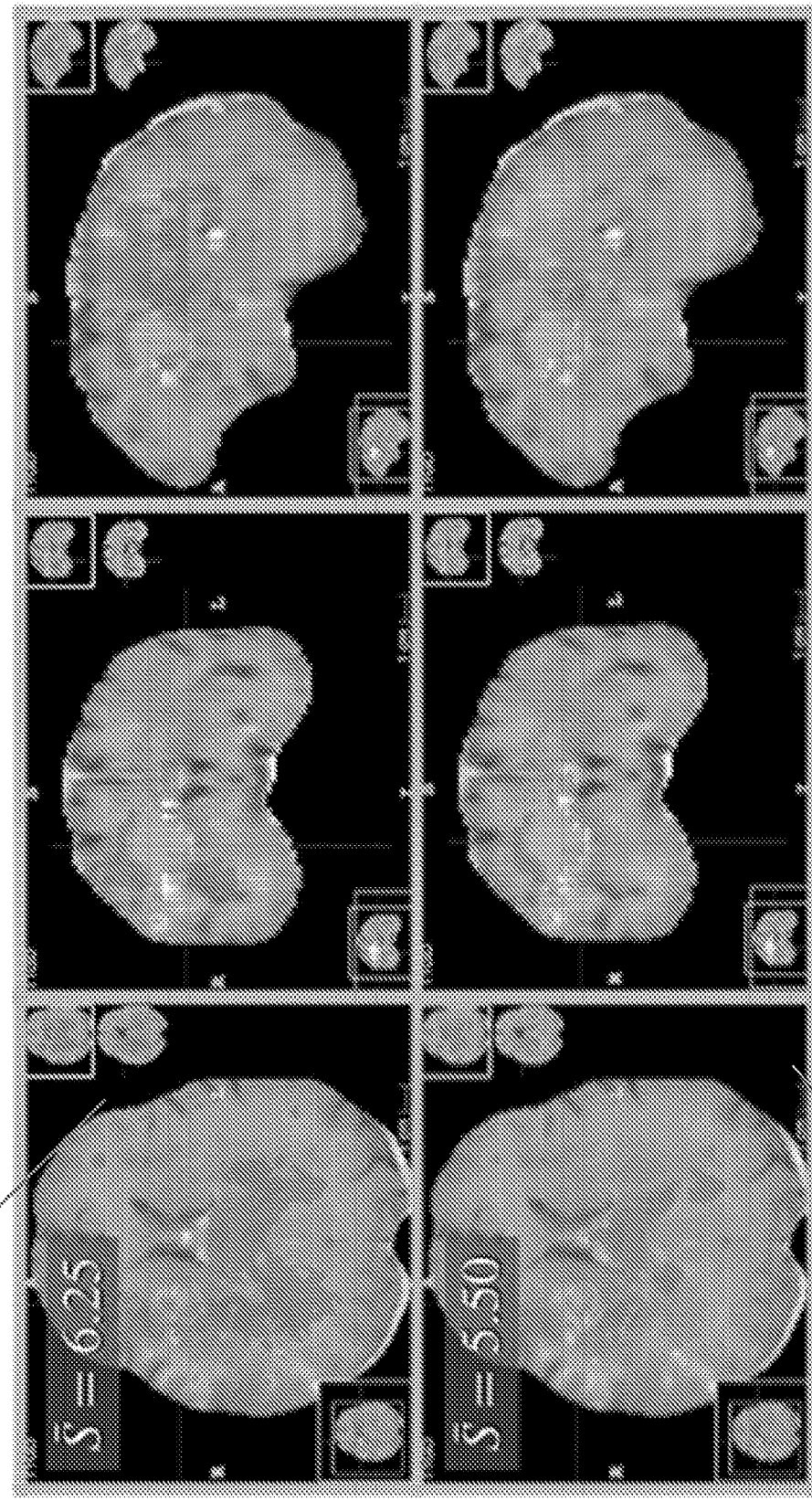
FIG. 2B shows a second set of images (Exam B with Dice=0.62) (T1c) from two test exams with the lowest Dice coefficients (poorest agreement between the technician and DeepMedic defined tumor regions) among the 100 test exams.
Figures 3A, 3B:
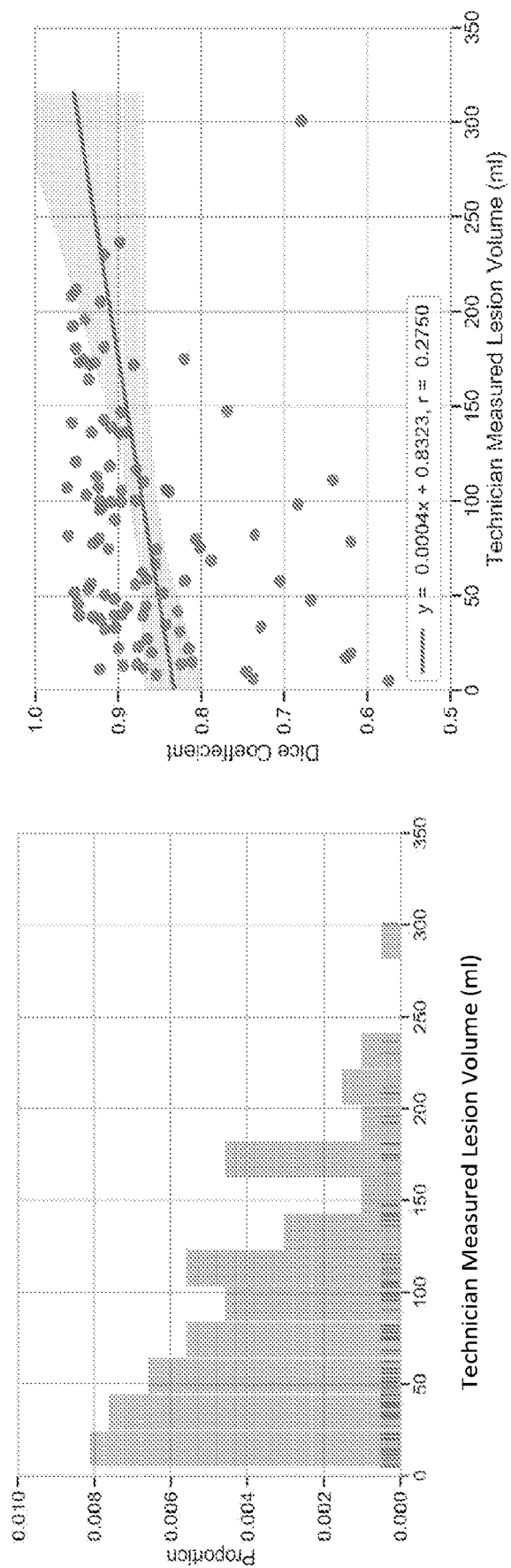
FIG. 3A shows one example distribution of technician measured tumor volumes.
FIG. 3B shows one example Dice coefficient plot of the tumor volumes of FIG. 3A.

The whole-tumor Dice coefficients between the technician and DL segmentations had a median value of 0.90 and a mean (±standard deviation) value of 0.87 (±0.08), over 100 test cases. The two test exams with the lowest Dice coefficients are shown in FIG. 2. FIG. 3a shows the distribution of technician measured lesion volumes. FIG. 3b shows the relationship between Dice coefficients and technician measured lesion volumes. This figure suggests a slight increase in Dice coefficient with increasing lesion volume (slope=0.0004), although the relationship is weak (r=0.2750).

Figure 4:
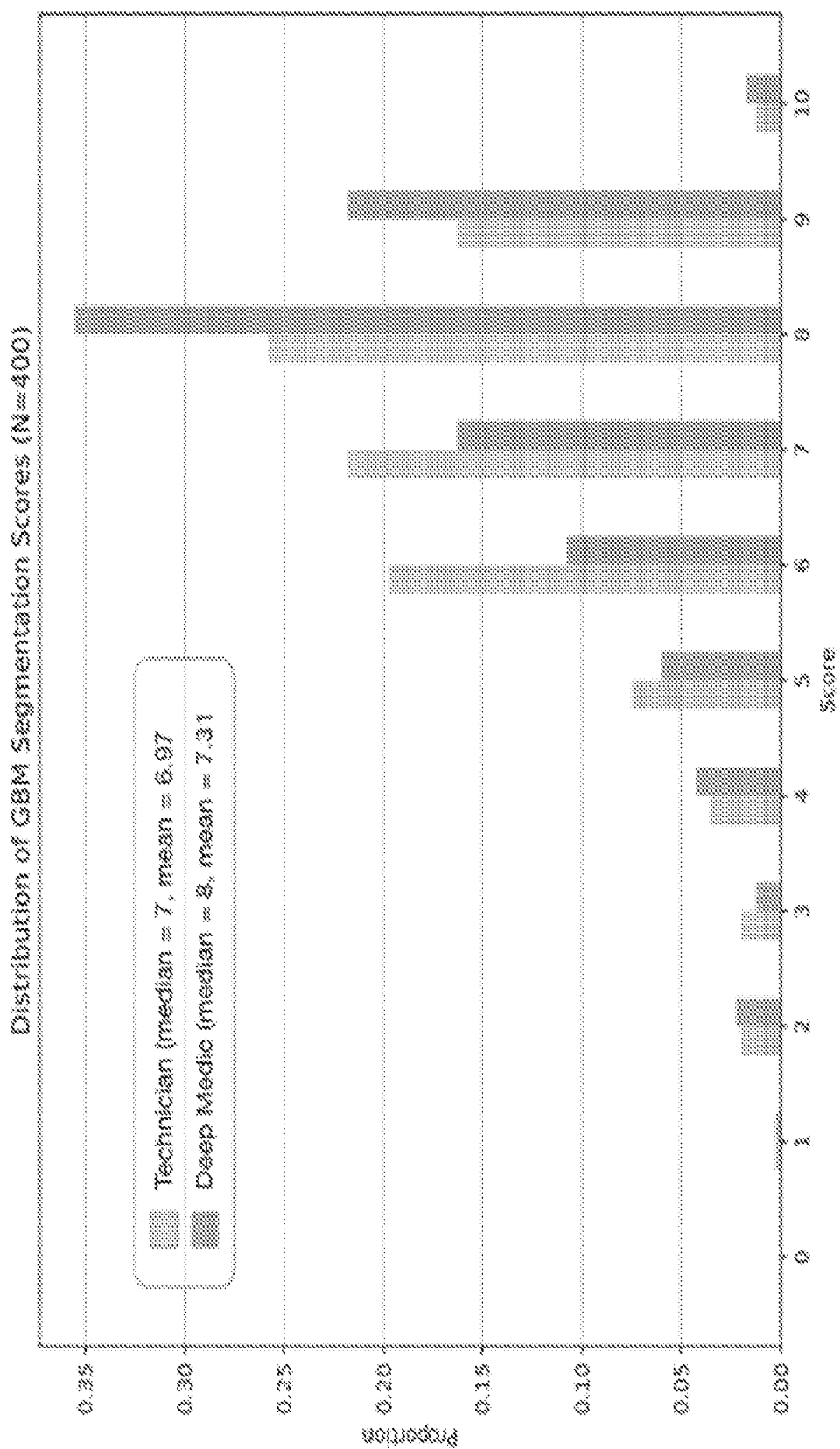
FIG. 4 shows the distribution of scores for manual technician and automatic deep learning (DL) segmentations in the test exams.
Figure 5A:
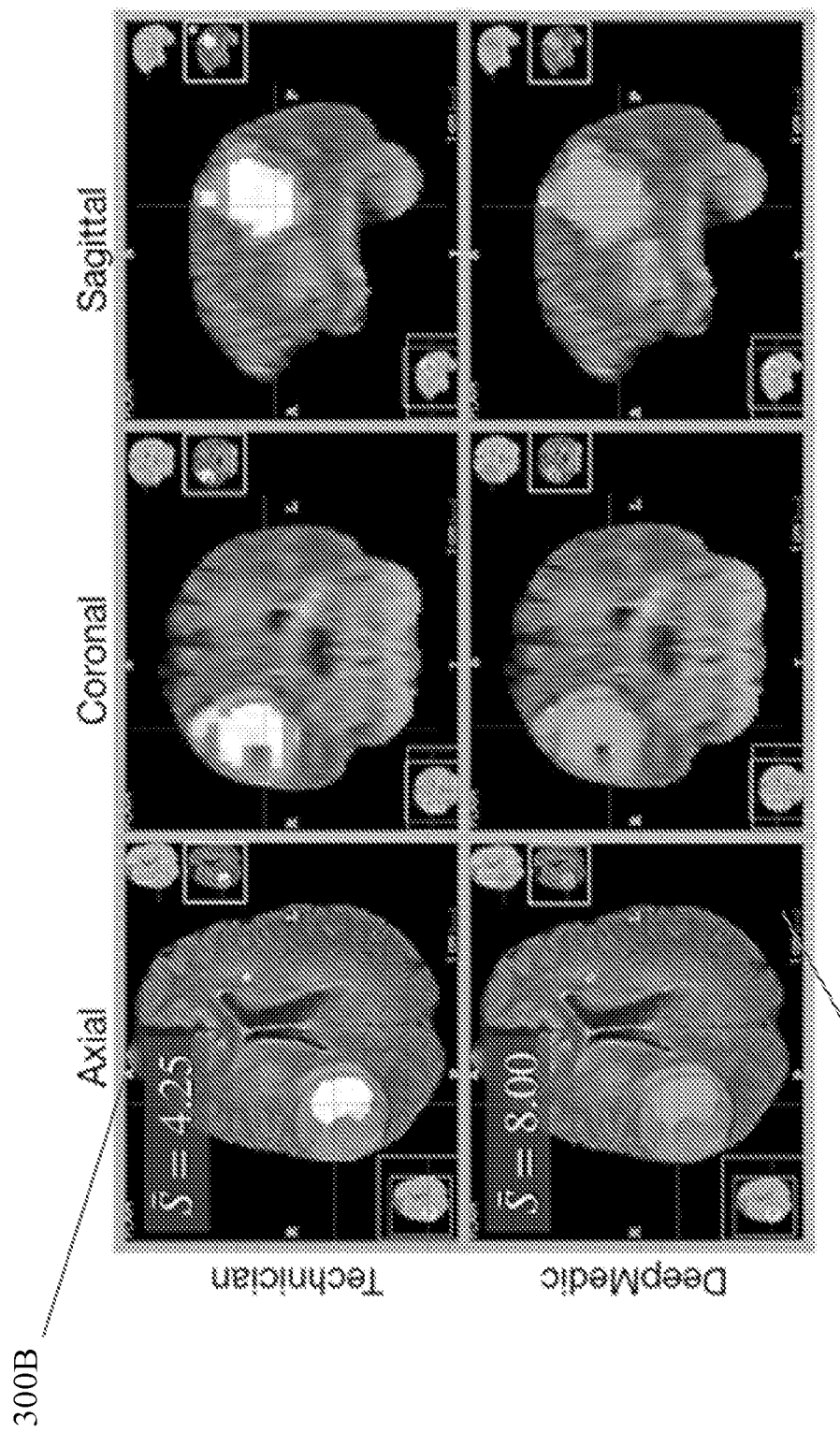
FIG. 5A shows a first of two test exams with the largest differences (deltas) between the neuroradiologist's mean scores for the technician and DeepMedic segmentations. This figure was labeled Exam C, Delta=−3.75, Dice=0.71, (FLAIR).
Figure 5B:
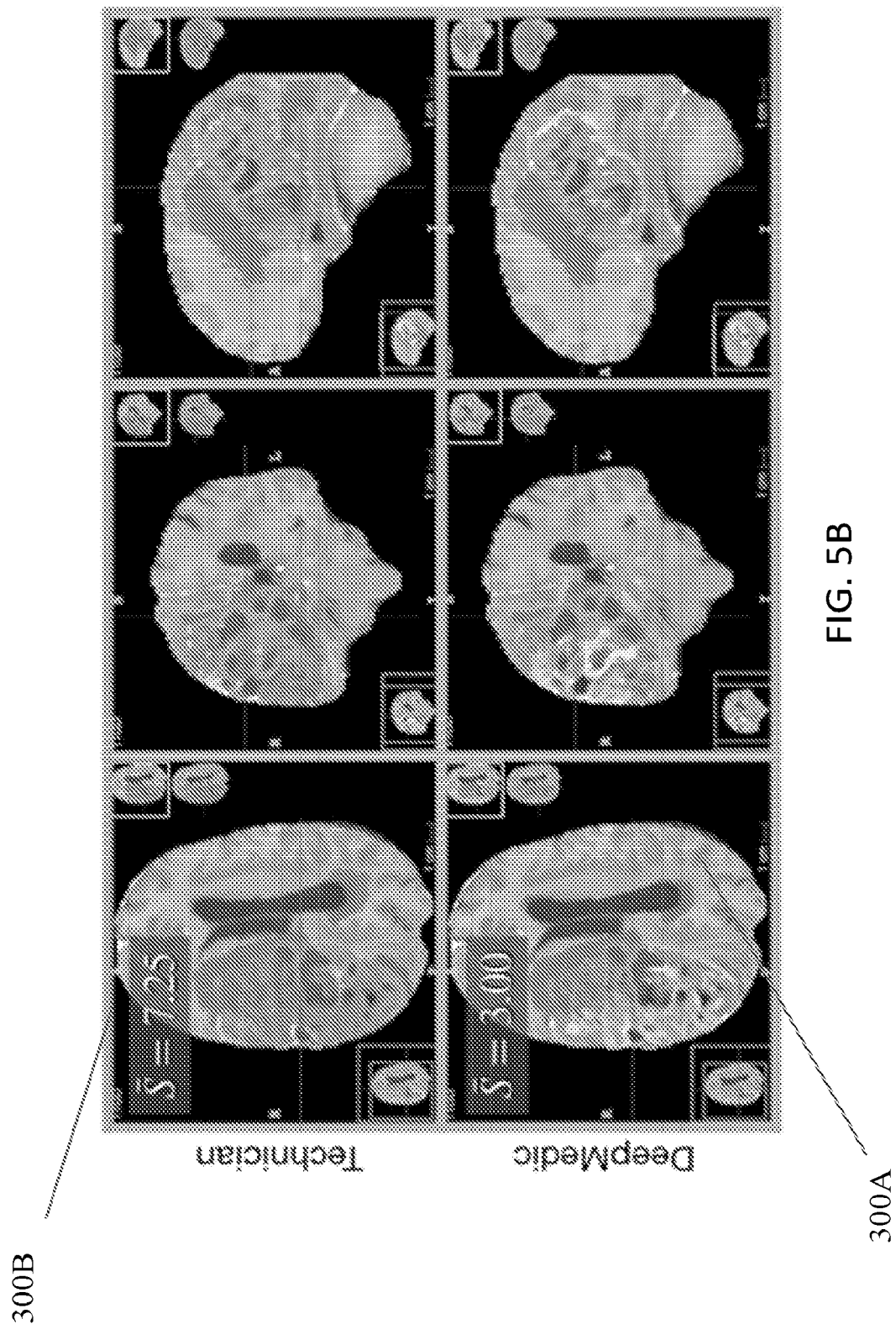
FIG. 5B shows a second of two test exams with the largest differences (deltas) between the neuroradiologist's mean scores for the technician and DeepMedic segmentations. This figure was labeled Exam D, Delta=+4.25, Dice=0.68, (T1c).
Figure 6:
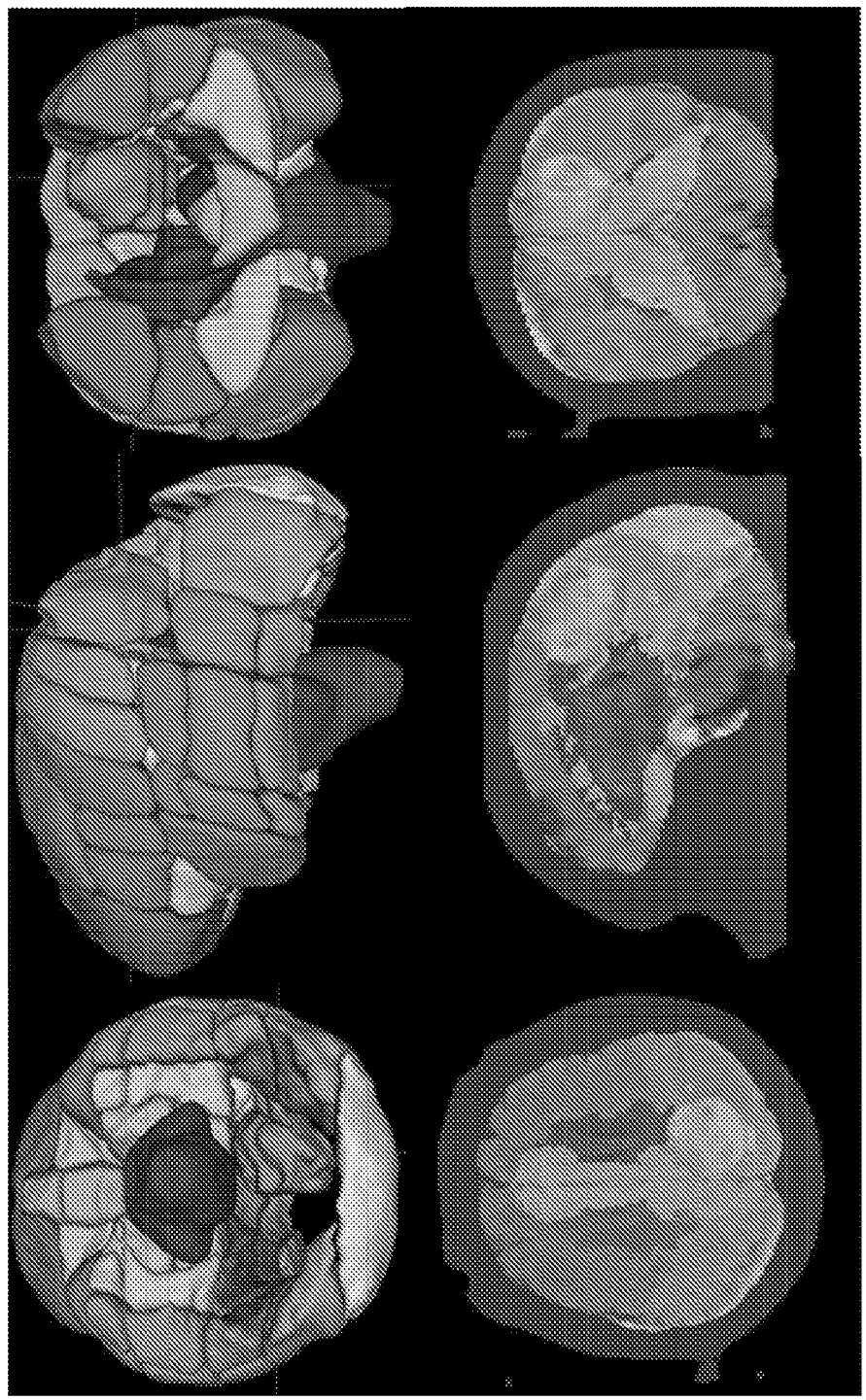
FIG. 6 is an example output from a Deep-Learning system for automatic brain tumor segmentation.

The neuroradiologist scores for the technician and DL segmentations had median values of 7 and 8, and mean values of 6.97 (±1.16) and 7.31 (±1.29), respectively (FIG. 4). The magnitude difference in the mean scores was 0.34. This value was different from 0 with a 2-sided p-value <0.00007. The two test exams with the largest differences between the neuroradiologist's mean scores for the technician and DL segmentations are shown in FIG. 5. FIG. 6 shows an example output from one non-limiting processing pipeline.

TABLE 2

The different types of brain tumors, and their frequencies, as reported in the patient cohort.

| | Tumor Type | N | % |
|---|---|---|---|
| | Glioblastomas | 463 | 62.5% |
| 1 | Glioblastoma Multiforme | 449 | |
| 2 | Glioblastoma Multiforme with Oligodendroglial Component | 7 | |
| 3 | Giant Cell Glioblastoma | 4 | |
| 4 | Glioblastoma Multiforme, Small Cell Type | 2 | |
| 5 | Glioblastoma Multiforme with Sarcomatous Differentiation | 1 | |
| | Astrocytomas | 77 | 10.4% |
| 6 | Astrocytoma | 38 | |
| 7 | Anaplastic Astrocytoma | 28 | |
| 8 | Diffuse Astrocytoma | 7 | |
| 9 | Infiltrating Fibrillary Astrocytoma | 2 | |
| 10 | Gemistocytic Astrocytoma | 1 | |
| 11 | Pleomorphic Xanthoastrocytoma | 1 | |
| | Oligodendrogliomas | 37 | 5.0% |
| 12 | Oligodendroglioma | 27 | |
| 13 | Anaplastic OligodendroGlioma | 10 | |
| | Mixed and Other | 19 | 2.5% |
| 14 | Anaplastic OligoAstrocytoma | 9 | |

TABLE 2-continued

The different types of brain tumors, and their frequencies, as reported in the patient cohort.

| | Tumor Type | N | % |
|---|---|---|---|
| 15 | Gliosarcoma | 5 | |
| 16 | OligoAstrocytoma | 2 | |
| 17 | GanglioGlioma | 1 | |
| 18 | Diffuse Pontine Intrinsic Glioma | 1 | |
| 19 | Low Grade Glioma | 1 | |
| | Not Specified | 145 | 19.6% |
| | Total | 741 | 100% |

Consolidating all of the above referenced details, FIG. 1 shows brain tumor segmentation review software, running on Amazon Web Services ("AWS") AppStream 2.0. AppStream allows the developer to run Windows in a virtual machine on AWS, and display the output to a remote instance of Google Chrome. Any application that can be installed in Windows can be installed in the virtual machine. This study developed an application in Python 3.6, and QT 5. The program launched two instances of ITK-SNAP (windows top right and top left) to display an MRI exam from the test set along with the manual technician and automatic DL tumor segmentations (red overlays). The order of the display is randomized, and the viewer is blinded to the source of the segmentation. Lesion "A" is always displayed in the top left window, and Lesion "B" in the top right. The viewer can zoom in and out, and move the cursor (crosshairs) to any location in the MRI volume. The two ITK-SNAP instances are synchronized so that they show the same location at all times. The bottom window provides widgets (sliders) that allow the viewer to quickly and easily score the quality of each segmentation. The bottom window also provides widgets that allow the viewer to move forward (or backward) through the MR exams in their assigned group of exams FIG. 2 shows the two test exams with the lowest Dice coefficients (poorest agreement between the technician and DeepMedic defined tumor regions) among the 100 test exams. Tumor segmentations are indicated in red. The mean neuroradiologist score for each exam, S⁻, is displayed in the top left corner of the axial view. Exam A (top two rows) had the lowest Dice coefficient among the 100 test exams. The disagreement between the two segmentation sources occurred primarily in the periventricular regions. There the technician labeled hyperintense regions as tumor, while DeepMedic did not. Periventricular hyperintensities are linked to small blood vessel disease and increased risk of stroke and dementia (36). Their prevalence increases with age in the general population. However, they typically are not associated with neoplasia. Exam B (bottom two rows) was tied with another exam (not shown) for the second lowest Dice coefficient. The disagreement in Exam B was widespread. Both segmentations missed areas of enhancement in the T1c scan.

FIG. 3 shows the distribution of, and Dice coefficients for, technician measured tumor volumes. a) shows the distribution of tumor volumes. These ranged from 5.07 ml to 300.84 ml, with a mean (±standard deviation) of 88.98 (±62.68) ml. The median technician measured tumor volume was 78.20 ml. b) shows a linear regression (blue line) between Dice coefficients and technician measured tumor volumes. This fit suggests a slight increase in Dice coefficient with increasing lesion volume (slope=0.0004). However, this relationship is weak (r=0.2750). The shaded blue region indicates the 95% confidence interval of the linear regression.

FIG. 4 shows the distribution of scores for manual technician and automatic deep learning (DL) segmentations in the test exams. Twenty neuroradiologists each performed 20 blinded and randomized side-by-side comparisons of the technician and DL segmentations in the 100 test exams. Scores ranged from 0 (no overlap with the MRI visible tumor) to 10 (perfect match with the MRI visible tumor). The technician and DL segmentations had median scores of 7 and 8, and mean (±standard deviation) scores of 6.97±1.16 and 7.31±1.29, respectively. The magnitude difference in the mean scores was 0.34. This value was different from 0 with a 2-sided p-value <0.00007. Additional details provided in the text.

FIG. 5 shows the two test exams with the largest differences (deltas) between the neuroradiologist's mean scores for the technician and DeepMedic segmentations. Tumor segmentations are indicated in red. The mean neuroradiologist score for each exam, S⁻, is displayed in the top left corner of the axial view. Delta is defined as: _S_ Technician-_S_DeepMedic Exam C (top two rows) had the largest score difference in favor of the DeepMedic segmentation. The technician did not label the enhancing core of the tumor in Exam C. Exam D (bottom two rows) had the largest score difference in favor of the technician segmentation. DeepMedic did not label extensive regions of enhancement in the T1c scan in Exam D.

FIG. 6 shows an example output from a Deep-Learning system for automatic brain tumor segmentation. The system loads an MRI exam containing a T1 weighted post-contrast scan (T1c) and a Fluid Attenuated Inversion Recovery (FLAIR) scan. Input from a wide range of MRI scanners, and with varying scan parameters, will work. The developers herein designed the system to perform the following steps automatically, without additional input: 1) enhance the MRI scans to remove artifacts; 2) identify the brain within the MRI scan (strip the skull), even in the presence of significant pathology or surgical interventions; 3) segment the brain tumor; and, 4) coregister the Harvard-Oxford probabilistic atlas to the brain. The last step is used for visualization purposes, and is optional. In this image, the tumor is red. Other colors indicate various atlas regions. The top and bottom row show 3D and 2D views of the output data, respectively. Several atlas regions in the vicinity of the tumor have been made transparent in the 3D view to aid tumor visualization.

Figure 7:
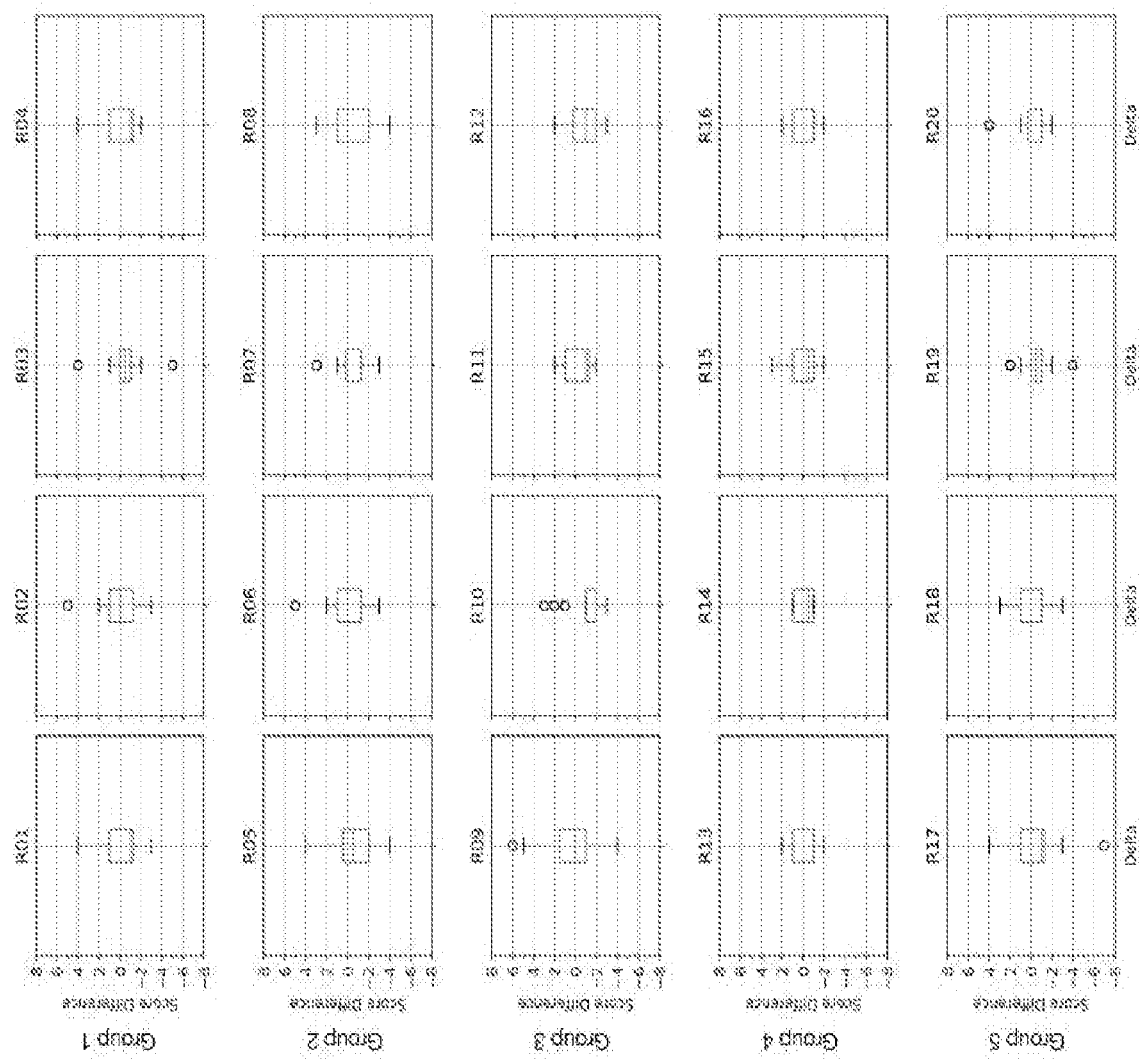
FIG. 7 illustrates boxplots showing the distribution of assigned radiologists' score differences, by test group.

FIG. 7 shows Boxplots showing the distribution of radiologist's score differences, by test group. The R numbers correspond to individual radiologists. For example, R01 refers to radiologist #1. Each row of plots corresponds to a specific group of 20 test exams. Thus, radiologists R01 through R04 all scored the same 20 exams in Group 1. The score difference is defined as the radiologist score for the technician segmentation minus the radiologist score for the DL segmentation. Negative values indicate that the DL segmentation was assigned a higher (better) score than the technician segmentation. Each box shows the range of data values between the first and third quartiles. The horizontal line within each box indicates the median value. The whiskers indicate the range of values. Outliers are indicated by small circles beyond the whiskers. Variability between radiologists, both within and between groups, is evident as differing box sizes and whisker lengths.

Discussion:

Recently, several groups have reported results from DL systems for brain tumor segmentation (Table 3). The accuracy of these, and prior, systems has generally been assessed by measuring the overlap with manual segmentations. The most commonly reported metric is the Dice coefficient. There are limitations with this approach—manual labeling is challenging and subject to variability. Also, even well trained and experienced technicians occasionally make mistakes (see FIGS. 2 and 5). Hence measures such as Dice may not accurately reflect real quality.

Therefore, an important contribution of this work was to evaluate the quality of the DL segmentations via the first comprehensive and objective comparison of automated and human segmentation using a blinded controlled assessment study. On average, the neuroradiologists scored the automated DL segmentations higher (better) than the manual technician segmentations by 0.34 points on a 10-point scale. This difference had a p-value <0.00007.

Current top performing systems tend to have median and mean Dice coefficients near 0.92 and 0.88, respectively (Table 3). All of the experiments listed in the Table made use of 4 MRI sequences, except this study discussed herein, which used only 2. One non-limiting experiment utilized a state-of-the-art brain tumor segmentation system. Consequently, researchers suspect that the additional information provided by 4 sequences may be responsible for the 1%-2% improvement in mean Dice coefficient over the current results. On the other hand, requiring only 2 input sequences should make the method more practical in clinical workflows.

Review of the 741 exams, after training and testing were complete, revealed that exam quality varied. The dataset includes exams with motion artifacts, aliasing artifacts, minimal attenuation of the fluid signal in some FLAIR sequences, occasional unconventional orientations of the head inside the MRI scanner, and variation in the MRI acquisition parameters. The diversity of training data provides some assurance that the methods disclosed herein will be translatable (29), at least for segmentation of pretreatment lesions. Future work will include training DeepMedic with exams from a database acquired throughout treatment and follow-up.

This study did not evaluate the performance of the network using the BraTS challenge dataset. This is because both the instant study dataset and the BraTS dataset contain a significant number of common MRI exams—those from The Cancer Imaging Archive (TCIA) and The Cancer Genome Atlas Glioblastoma Multiforme (GBM) data collections (TCGA-GBM) (30). Differences in the naming conventions between the BraTS dataset and this study prevented us from determining correspondence between specific MRI exams in the two datasets. Thus, there was a high likelihood that studies used to train the network were present in the BraTS data. Using the trained network to segment tumors in the BraTS dataset would have produced biased results.

This study observed within- and between-radiologist scoring variability (FIG. 7). Consequently, the score differences between the technician and DL segmentations are likely to be even larger than suggested, if these differences are real (31). To determine the effects of scoring variability, and the degree of agreement between all of the radiologists, one would need to perform a replication study, where multiple radiologists perform multiple repeated scores on a large number of segmentations. But ultimately, the challenge lies in the relative subjectivity intrinsic in human (even expert neuroradiologist) assessment.

The blinded controlled assessment study discussed herein indicates that a deep learning ("DL") system produced higher-quality segmentations, on average, than the technicians who created the training labels. This observation appears to contradict the widely held belief that a model is only as good as the data used to train it. It should be noted, however, that it is very difficult to determine the exact border of a cellularly diffuse and invasive tumor in the brain of a living patient. Consequently, training labels likely include imperfections. The relationships between model accuracy, the number of training samples, and the effects of imperfect, or "noisy" training labels, have been studied extensively (32-35). These studies show that in general, models achieve higher accuracy than the average accuracy of the training labels (provided that the labels have >50% accuracy). For example, Sheng et. al. (32) demonstrated an example where 70% accurate labels were used to train a model that achieved 90% accuracy when applied to a sequestered test set with perfect labels. In the same publication, 80% accurate labels produced a model with near-perfect accuracy on the test set.

Table 3 below shows the Dice coefficients for the Heidelberg datasets for contrast-enhancing tumor regions. Dice coefficients for all other entries are for whole tumor segmentation. "MRI Series" is the number of series required as input. "Val. Set Size" refers to the validation set size. The first three deep nets were the top scoring solutions for the Multimodal Brain Tumor Segmentation (BraTS) challenge from 2017. Networks 4 through 7 were the top-scoring solutions from BraTS 2018. The Heidelberg solution was trained using a 5-fold cross-validation on 455 exams, ie, the dataset was divided into 5 groups of 91 exams each. In each fold, 4 of these groups (364 exams) were used for training, and 1 group (91 exams) was used for validation. The resulting 5 deep neural networks were then used as an ensemble to segment a separate sequence of 239 exams from the same institution. Then, the Heidelberg ensemble was used to segment 2034 exams acquired from 38 institutions as part of a clinical trial (EORTC). DeepMedic is our ensemble of 5 networks applied to 100 of our test studies.

TABLE 3

The agreement between manual and deep learning tumor segmentation, expressed as the mean or median Dice Coefficient over the test set, for multiple neural nets.

| | Neural Network | Dataset | MRI Series | Ensemble Size | Training Set Size | Val. Set Size | Test Set Size | Test Median Dice | Test Mean Dice |
|---|---|---|---|---|---|---|---|---|---|
| 1 | EMMA(12) | BraTS 2017 | 4 | 21 | 285 | 46 | 146 | n/a | 0.88 |
| 2 | Cascaded CNNs(11) | BraTS 2017 | 4 | 9 | 285 | 46 | 146 | n/a | 0.87 |
| 3 | Brain Tumor U-Net(13) | BraTS 2017 | 4 | 15 | 285 | 46 | 146 | n/a | 0.86 |
| 4 | NVDLMED(37) | BraTS 2018 | 4 | 10 | 285 | 66 | 191 | 0.92 | 0.88 |
| 5 | MIC-DKFZ(38) | BraTS 2018 | 4 | 10 | 285 | 66 | 191 | 0.92 | 0.88 |
| 6 | DeepSCAN(39) | BraTS 2018 | 4 | 12 | 285 | 66 | 191 | 0.92 | 0.89 |
| 7 | DL_86_61(40) | BraTS 2018 | 4 | 7 | 285 | 66 | 191 | 0.92 | 0.88 |
| 8 | Heidelberg(14) | Heidelberg EORTC | 4 | 5 | 364 | 91 | 2273 | 0.89-0.91 | n/a |
| 9 | DeepMedic | This study | 2 | 5 | 641 | 0 | 100 | 0.90 | 0.87 |

Finally, this study suggests that there may be new ways to use finite image labeling resources (limited by time and/or budget) to produce models with better overall performance. For example, rather than acquire a few high-quality segmentations, it may be better to acquire a larger number of lower-quality segmentations with additional repeated segmentations per lesion. The success of new strategies will depend upon many factors, including: lesion complexity, the experience of the people performing the segmentations, the number of segmentations, and the methods used to extract information from repeated measurements. Additional studies are required to investigate the effects of these factors on model performance.

To date, this is the first time this phenomenon has been demonstrated in a medical image segmentation task. There are several interesting ramifications. First, perfect or near-perfect training labels may not be required to produce high-performing segmentation systems. This could be important for any medical image segmentation task where near-perfect labels are difficult, time-consuming and/or costly to obtain. Second, the prior studies show that when labels are imperfect there are advantages to obtaining multiple labels for each training sample. Furthermore, there are several methods to combine information from repeated labeling to improve model performance.

Data Availability:

The data used in this study (741 MRI exams) are part of a larger collection curated by the Department of Neurosurgery, Mayo Clinic Arizona. These data contain protected health information and are therefore subject to HIPAA regulations. While platforms may exist to completely de-identify images, the resources are not currently available to complete that process. Thus, sharing of images requires additional constraints to ensure protection of patient privacy. Typically, access to this type of data (inclusive of images) occurs through a collaboration and may require interested parties to obtain an affiliate appointment with Mayo Clinic and/or require a data sharing agreement. Data that is shared will include standards and notations needed to interpret the data, following commonly accepted practices in the field.

Embodiments of this work include a computer implemented method of determining accuracy of a neural network in producing computerized segmentations within magnetic resonant (MR) images 100A, 100B. The steps of the method include saving computer segmented images on a first computer 200 connected to a network 216. The first computer 200 communicates with test computers 250A-250$n$ connected to the network 216, wherein the test computers 250A-250$n$ display the computer segmented images 300A alongside manually segmented test images 300B for scoring. In return, the first computer 200 receives scores 150A, 150B for the accuracy of the manually segmented test images 300B and the computer segmented images 300A from the test computer.

To enable scoring, the test computers 250A-250$n$ access manually segmented images 300B that have been saved on respective technician computers 230A-230$n$ in respective memory, and the test computers 250A-250$n$ display at least one manually segmented test image 300B and at least one computer segmented image 300A on the test computer in a series. The images 100A, 100B are shown in randomly ordered pairs in a blind identification process.

The computerized method further includes using a trained human (the above described radiologists) to compare the manually segmented test image 300B and the computer segmented image 300A with a display 105 connected to the test computer 250A-250$n$, wherein the trained human scores, for accuracy, segmentations 125 present in the computer segmented images and the manually segmented test images, without knowledge of which image is computer segmented or manually segmented. As described in the method described above, identical sets of manually segmented test images and computer segmented images may be evaluated by multiple trained humans for scoring in a blind randomized process.

Without limiting the disclosure in any way, the computerized method includes displaying, on the test computer, MR images having at least one of axial, sagittal, and coronal views with segmentations displayed as a respective translucent overlay thereon. The radiologist may compare series of respective manually segmented test images and the computer segmented images with a display connected to the test computer, wherein the radiologist sends the score to the first computer over the network, and wherein the score comprises a selection of one numerical score from a scale including 0: No Match, 2: Very Poor Match, 4: Poor Match, 6: Good Match, 8: Very Good Match, 10: Perfect Match.

This disclosure may also be embodied in a computer implemented system of determining accuracy of a neural network in producing computerized segmentations within magnetic resonant (MR) images. the MR images used as inputs to the neural network are pre-treatment images of a subject.

The system may include a segmenting computer 150 having a processor connected to computerized memory storing software implementing the neural network, the computerized memory storing adjustable settings for neural network configuration parameters, wherein the segmenting computer 150 receives the MR images 100A, 100B as inputs to the neural network and segments regions 125 within the MR images 100A, 100B with the neural network to produce computer segmented images 300A. The segmenting computer 150 may connect to and run multiple instances of the neural network for image segmentation. The segmenting computer 150 initializes each of the multiple instances of the neural network with respectively randomized weight parameters during a training phase of the neural network, prior to receiving the inputs of the MR images 100A, 100B to be segmented. A training phase of utilizing the neural network comprises computing Dice coefficients of the manually segmented images and the computer segmented images.

A first computer 200 is connected over the network 216 to the segmenting computer 150, wherein the first computer 200 saves the computer segmented images received from the segmenting computer. The first computer 200 communicates with test computers 250A-250$n$ connected to the network 216, wherein the test computers display the computer segmented images 300A alongside manually segmented test images 300B for scoring. The first computer also receives scores 150A, 150B from the test computers 250A-250$n$ detailing the accuracy of the manually segmented test images and the computer segmented images. These scores indicate necessary adjustments to the neural network and using the segmenting computer, technicians update the neural network configuration parameters after receiving the scores. In one embodiment, the neural network configuration parameters include at least a number of training epochs and a learning rate step decay schedule.

The system of this disclosure also includes technician computers 230A-230$n$ facilitating manual segmenting steps to produce the manually segmented images and storing the manually segmented images in the first computer connected to the network. The manually segmented test images 300B were pre-processed to form a consensus segmentation from multiple segmentations of the same image.

The system includes scoring software saved in respective memory of the test computers 250A-250$n$, wherein the software retrieves the computer segmented images 300A and the manually segmented images 300B over the network. The scoring software comprises a scoring mechanism for entering scores for the manually segmented test images and the computer segmented test images. In one non-limiting example, the scoring mechanism is a slider scale as shown in FIG. 1 and configured to enter one numerical score from a scale including 0: No Match, 2: Very Poor Match, 4: Poor Match, 6: Good Match, 8: Very Good Match, 10: Perfect Match.

Figure 8:
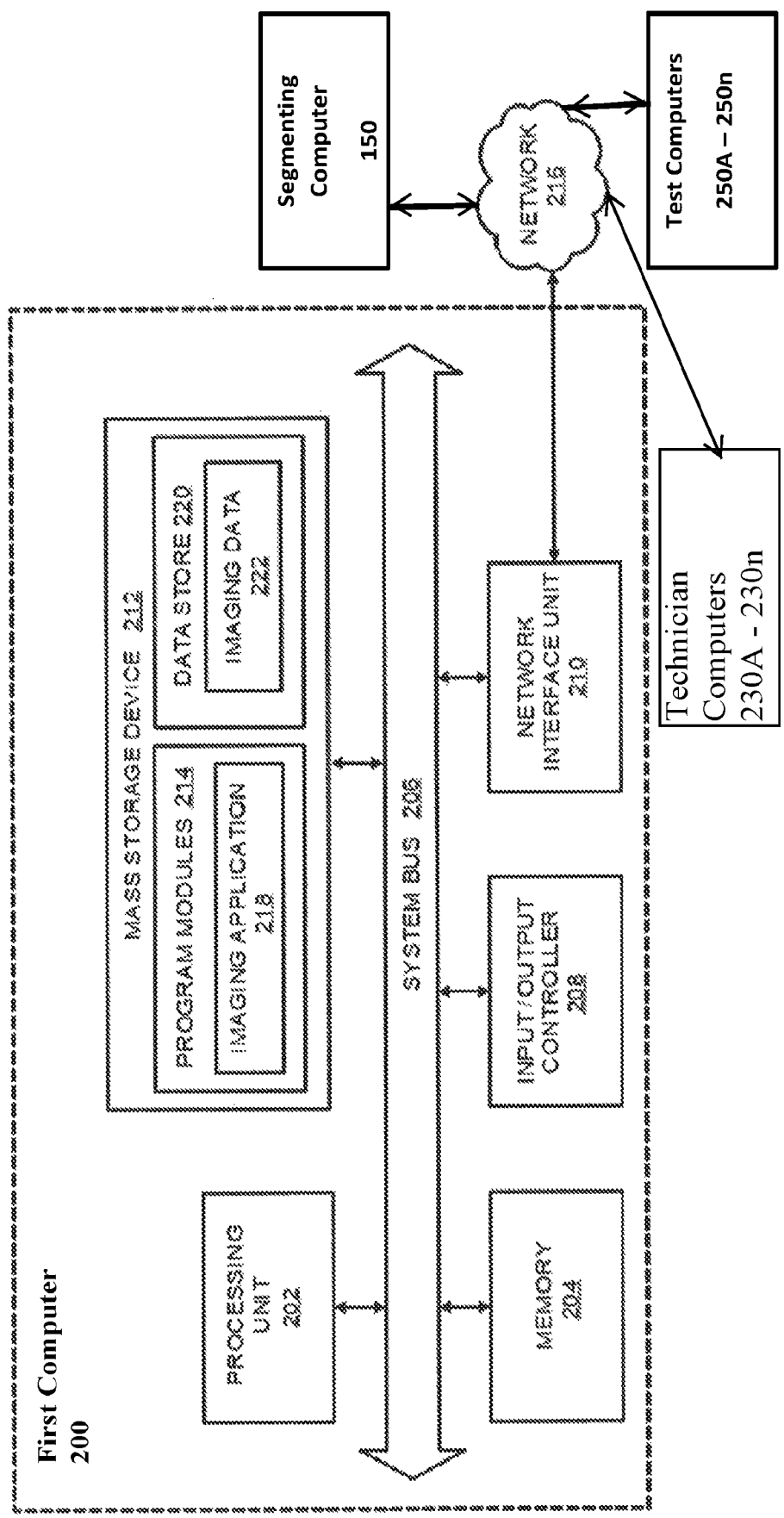
FIG. 8 is a schematic of computer systems connected to a network and utilizing the computerized methods of this disclosure.

FIG. 8 is a computer architecture diagram showing a general computing system capable of implementing aspects of the disclosed technology in accordance with one or more embodiments described herein. All of the computers used in this disclosure have appropriate processing power and hardware to accomplish the tasks at hand. By way of example, a first computer 200 may be configured to perform one or more functions associated with embodiments illustrated in one or more of the other figures. It should be appreciated that the first computer 200 may be implemented within a single computing device or a computing system formed with multiple connected computing devices. The first computer 200 may be configured to perform various distributed computing tasks, in which processing and/or storage resources may be distributed among the multiple devices.

As shown, the first computer 200 includes a processing unit 202 ("CPU"), a system memory 204, and a system bus 206 that couples the memory 204 to the CPU 202. The computer 200 further includes a mass storage device 212 for storing program modules 214. The program modules 214 may be operable to perform associated with embodiments illustrated in one or more of the other figures. The program modules 214 may include an imaging application 218 for performing data acquisition and/or processing functions as described herein, for example to acquire and/or process image data corresponding to magnetic resonance imaging of an area of interest. The computer 200 can include a data store 220 for storing data that may include imaging-related data 222 such as acquired data from the implementation of magnetic resonance imaging in accordance with various embodiments of the disclosed technology.

The mass storage device 212 is connected to the CPU 202 through a mass storage controller (not shown) connected to the bus 206. The mass storage device 212 and its associated computer-storage media provide non-volatile storage for the computer 200. Although the description of computer-storage media contained herein refers to a mass storage device, such as a hard disk or CD-ROM drive, it should be appreciated by those skilled in the art that computer-storage media can be any available computer storage media that can be accessed by the first computer 200.

The test computers 250A-250n, the segmenting computer(s) 150, and the technician computers 230A-230n all have similar hardware as described for the first computer but may have additional software and hardware capabilities to complete assigned tasks described herein.

By way of example and not limitation, computer storage media (also referred to herein as "computer-readable storage medium" or "computer-readable storage media") may include volatile and non-volatile, removable and non-removable media implemented in any method or technology for storage of information such as computer-storage instructions, data structures, program modules, or other data. For example, computer storage media includes, but is not limited to, RAM, ROM, EPROM, EEPROM, flash memory or other solid state memory technology, CD-ROM, digital versatile disks ("DVD"), HD-DVD, or other optical storage, magnetic cassettes, magnetic tape, magnetic disk storage or other magnetic storage devices, or any other medium which can be used to store the desired information and which can be accessed by the first computer 200. "Computer storage media", "computer-readable storage medium" or "computer-readable storage media" as described herein do not include transitory signals.

According to various embodiments, the first computer 200 may operate in a networked environment using connections to other local or remote computers through a network 216 via a network interface unit 210 connected to the bus 206. The network interface unit 210 may facilitate connection of the computing device inputs and outputs to one or more suitable networks and/or connections such as a local area network (LAN), a wide area network (WAN), the Internet, a cellular network, a radio frequency (RF) network, a Bluetooth-enabled network, a Wi-Fi enabled network, a satellite-based network, or other wired and/or wireless networks for communication with external devices and/or systems. The computer 200 may also include an input/output controller 208 for receiving and processing input from any of a number of input devices. Input devices may include one or more of keyboards, mice, stylus, touchscreens, microphones, audio capturing devices, and image/video capturing devices. An end user may utilize the input devices to interact with a user interface, for example a graphical user interface, for managing various functions performed by the first computer 200. The bus 206 may enable the processing unit 202 to read code and/or data to/from the mass storage device 212 or other computer-storage media. The computer-storage media may represent apparatus in the form of storage elements that are implemented using any suitable technology, including but not limited to semiconductors, magnetic materials, optics, or the like. The computer-storage media may represent memory components, whether characterized as RAM, ROM, flash, or other types of technology.

The computer storage media may also represent secondary storage, whether implemented as hard drives or otherwise.

REFERENCES

1. Clarke L P, Velthuizen R P, Camacho M A, et al. MRI segmentation: methods and applications. Magn Reson Imaging. Elsevier; 1995; 13(3):343-68 https://www.ncbi.nlm.nih.gov/pubmed/7791545.
2. Vaidyanathan M, Clarke L P, Hall L O, et al. Monitoring brain tumor response to therapy using MRI segmentation. Magn Reson Imaging. Elsevier; 1997; 15(3):323-334https://www.ncbi.nlm.nih.gov/pubmed/9201680.
3. Magnotta V A, Heckel D, Andreasen N C, et al. Measurement of brain structures with artificial neural networks: two- and three-dimensional applications. Radiology. pubs.rsna.org; 1999; 211(3):781-790http://dx.doi.org/10.1148/radiology.211.3.r99ma07781.
4. Roberts M, Packer J, Sousa M C, Mitchell J R. A work-efficient GPU algorithm for level set segmentation. Proceedings of the Conference on High Performance Graphics. Eurographics Association; 2010. p. 123-132.
5. Moon N, Bullitt E, van Leemput K, Gerig G. Automatic Brain and Tumor Segmentation. Medical Image Computing and Computer-Assisted Intervention—MICCAI 2002. Springer Berlin Heidelberg; 2002. p. 372-379http://dx.doi.org/10.1007/3-540-45786-0_46.
6. Kaus M R, Warfield S K, Nabavi A, Black P M, Jolesz F A, Kikinis R. Automated segmentation of MR images of brain tumors. Radiology. pubs.rsna.org; 2001; 218(2): 586-591http://dx.doi.org/10.1148/radiology.218.2.r01fe44586.
7. Corso J J, Sharon E, Dube S, El-Saden S, Sinha U, Yuille A. Efficient multilevel brain tumor segmentation with integrated bayesian model classification. IEEE Trans Med Imaging. ieeexplore.ieee.org; 2008; 27(5):629-640http://dx.doi.org/10.1109/TMI.2007.912817.
8. Dang M, Modi J, Roberts M, Chan C, Mitchell J R. Validation study of a fast, accurate, and precise brain tumor volume measurement. Comput Methods Programs 9. Kamnitsas K, Ferrante E, Parisot S, et al. DeepMedic for Brain Tumor Segmentation. Lecture Notes in Computer Science. 2016. p. 138-149http://dx.doi.org/10.1007/978-3-319-55524-9_14.
10. Menze B H, Jakab A, Bauer S, et al. The Multimodal Brain Tumor Image Segmentation Benchmark (BRATS). IEEE Trans Med Imaging. 2015; 34(10):1993-2024http://dx.doi.org/10.1109/TMI.2014.2377694.
11. Wang G, Li W, Ourselin S, Vercauteren T. Automatic Brain Tumor Segmentation Using Cascaded Anisotropic Convolutional Neural Networks. Lecture Notes in Computer Science. 2018. p. 178-190http://dx.doi.org/10.1007/978-3-319-75238-9_16.
12. Kamnitsas K, Bai W, Ferrante E, et al. Ensembles of Multiple Models and Architectures for Robust Brain Tumor Segmentation. Lecture Notes in Computer Science. 2018. p. 450-462http://dx.doi.org/10.1007/978-3-319-75238-9_38.
13. Isensee F, Kickingereder P, Wick W, Bendszus M, Maier-Hein K H. Brain Tumor Segmentation and Radiomics Survival Prediction: Contribution to the BRATS 2017 Challenge. Lecture Notes in Computer Science. 2018. p. 287-297http://dx. doi. org/10.1007/978-3-319-75238-9_25.
14. Kickingereder P, Isensee F, Tursunova I, et al. Automated quantitative tumour response assessment of MRI in neuro-oncology with artificial neural networks: a multi-centre, retrospective study. Lancet Oncol. Elsevier; 2019; http://dx.doi.org/10.1016/S1470-2045(19)30098-1.
15. Shin H-C, Tenenholtz N A, Rogers J K, et al. Medical Image Synthesis for Data Augmentation and Anonymization using Generative Adversarial Networks. arXiv [cs.CV]. 2018.http://arxiv.org/abs/1807.10225.
16. Chang K, Beers A L, Bai H X, et al. Automatic assessment of glioma burden: A deep learning algorithm for fully automated volumetric and bi-dimensional measurement. Neuro Oncol. 2019; http://dx.doi.org/10.1093/neuonc/noz106.
17. Swanson K R. Mathematical modeling of the growth and control of tumors. 1999.
18. Marstal K, Berendsen F, Staring M, Klein S. SimpleElastix: A User-Friendly, Multi-lingual Library for Medical Image Registration. 2016 IEEE Conference on Computer Vision and Pattern Recognition Workshops (CVPRW). 2016.http://dx.doi.org/10.1109/cvprw.2016.78.
19. Sethian J A. Level set methods and fast marching methods: evolving interfaces in computational geometry, fluid mechanics, computer vision, and materials science. Cambridge university press; 1999.
20. Tustison N J, Avants B B, Cook P A, et al. N4ITK: improved N3 bias correction. IEEE Trans Med Imaging. 2010; 29(6):1310-1320http://dx.doi.org/10.1109/TMI.2010.2046908.
21. Roy S, Butman J A, Pham D L, Alzheimers Disease Neuroimaging Initiative. Robust skull stripping using multiple MR image contrasts insensitive to pathology. Neuroimage. 2017; 146:132-147http://dx.doi.org/10.1016/j.neuroimage.2016.11.017.
22. Desikan R S, Ségonne F, Fischl B, et al. An automated labeling system for subdividing the human cerebral cortex on MRI scans into gyral based regions of interest. Neuroimage. 2006; 31(3):968-980http://dx.doi.org/10.1016/j.neuroimage.2006.01.021.
23. van der Lijn F, de Bruijne M, Hoogendam Y Y, et al. Cerebellum segmentation in MRI using atlas registration and local multi-scale image descriptors. 2009 IEEE International Symposium on Biomedical Imaging: From Nano to Macro. ieeexplore.ieee.org; 2009. p. 221-224http://dx.doi.org/10.1109/ISBI.2009.5193023.
24. Mazziotta J C, Toga A W, Evans A, Fox P, Lancaster J, Others. A probabilistic atlas of the human brain: theory and rationale for its development. Neuroimage. ece.uvic.ca; 1995 ; 2(2): 89-101https://www.ece.uvic.ca/~bctill/papers/learning/Mazziotta_etal_1995. pdf
25. Mohamed A, Zacharaki E I, Shen D, Davatzikos C. Deformable registration of brain tumor images via a statistical model of tumor-induced deformation. Med Image Anal. Elsevier; 2006; 10(5):752-763http://dx.doi.org/10.1016/j.media.2006.06.005.
26. Dice L R. Measures of the amount of ecologic association between species. Ecology. 1945; 26(3):297-302.
27. Loshchilov I, Hutter F. SGDR: Stochastic Gradient Descent with Warm Restarts. arXiv [cs.LG]. 2016.http://arxiv.org/abs/1608.03983.
28. Yushkevich P A, Piven J, Hazlett H C, et al. User-guided 3D active contour segmentation of anatomical structures: significantly improved efficiency and reliability. Neuroimage. 2006; 31(3):1116-1128.
29. Zech J R, Badgeley M A, Liu M, Costa A B, Titano J J, Oermann E K. Variable generalization performance of a deep learning model to detect pneumonia in chest radiographs: A cross-sectional study. PLoS Med. 2018; 15(11): e1002683http://dx.doi.org/10.1371/journal.pmed.1002683.
30. Clark K, Vendt B, Smith K, et al. The Cancer Imaging Archive (TCIA): maintaining and operating a public information repository. J Digit Imaging. Springer; 2013; 26(6):1045-1057http://dx.doi.org/10.1007/s10278-013-9622-7.
31. Riggs D S, Guarnieri J A, Addelman S. Fitting straight lines when both variables are subject to error. Life Sci. Elsevier; 1978; 22(13-15):1305-1360https://www.ncbi.nlm.nih.gov/pubmed/661506.
32. Sheng V S, Provost F, Ipeirotis P G. Get another label? improving data quality and data mining using multiple, noisy labelers. Proceeding of the 14th ACM SIGKDD international conference on Knowledge discovery and data mining—KDD 08. 2008.http://dx.doi.org/10.1145/1401890.1401965.
33. Ipeirotis P G, Provost F, Sheng V S, Wang J. Repeated labeling using multiple noisy labelers. Data Mining and Knowledge Discovery. 2014. p. 402-441http://dx.doi.org/10.1007/s10618-013-0306-1.
34. Zheng Y, Scott S, Deng K. Active Learning from Multiple Noisy Labelers with Varied Costs. 2010 IEEE International Conference on Data Mining. 2010.http://dx.doi.org/10.1109/icdm.2010.147.
35. Sheng V S. Simple Multiple Noisy Label Utilization Strategies. 2011 IEEE 11th International Conference on Data Mining. 2011.http://dx.doi.org/10.1109/icdm.2011.133.
36. Debette S, Markus H S. The clinical importance of white matter hyperintensities on brain magnetic resonance imaging: systematic review and meta-analysis. BMJ. bmj.com; 2010; 341:c3666http://dx.doi.org/10.1136/bmj.c3666.
37. Myronenko A. 3D MRI Brain Tumor Segmentation Using Autoencoder Regularization. Brainlesion: Glioma, Multiple Sclerosis, Stroke and Traumatic Brain Injuries.

Springer International Publishing; 2019. p. 311-320 http://dx.doi.org/10.1007/978-3-030-11726-9_28.
38. Isensee F, Kickingereder P, Wick W, Bendszus M, Maier-Hein K. No New-Net: 4th International Workshop, BrainLes 2018, Held in Conjunction with MICCAI 2018, Granada, Spain, Sep. 16, 2018, Revised Selected Papers, Part II. 2019. p. 234-244 http://dx.doi.org/10.1007/978-3-030-11726-9_21.
39. McKinley R, Meier R, Wiest R. Ensembles of Densely-Connected CNNs with Label-Uncertainty for Brain Tumor Segmentation. Brainlesion: Glioma, Multiple Sclerosis, Stroke and Traumatic Brain Injuries. Springer International Publishing; 2019. p. 456-465 http://dx.doi.org/10.1007/978-3-030-11726-9_40.
40. Zhou C, Chen S, Ding C, Tao D. Learning Contextual and Attentive Information for Brain Tumor Segmentation. Brainlesion: Glioma, Multiple Sclerosis, Stroke and Traumatic Brain Injuries. Springer International Publishing; 2019. p. 497-507 http://dx. doi. org/10.1007/978-3-030-11726-9_44.
41. Çiçek, Ö., Abdulkadir, A., Lienkamp, S. S., Brox, T. and Ronneberger, O., 2016, October. 3D U-Net: learning dense volumetric segmentation from sparse annotation. In International Conference on Medical Image Computing and Computer-Assisted Intervention (pp. 424-432). Springer International Publishing.

The invention claimed is:

1. A computer implemented method of determining accuracy of a neural network in producing computerized segmentations within magnetic resonant (MR) images, comprising:
    saving computer segmented images on a first computer connected to a network;
    communicating with test computers connected to the network, wherein the test computers display the computer segmented images alongside manually segmented test images for scoring; and
    receiving, at the first computer, scores for the accuracy of the manually segmented test images and the computer segmented images from the test computer; and
    displaying at least one manually segmented test image and at least one computer segmented image on at least one of the test computers in a series, in random order, and in a blind identification process.

2. The method of claim 1, further comprising saving the manually segmented test images on the first computer.

3. The method of claim 1, further comprising computing the scores for the accuracy by displaying the computer segmented images and the manually segmented test images on a display connected to a respective test computer and comparing segmentations present in the computer segmented images and the manually segmented test images, without knowledge of which image is computer segmented or manually segmented.

4. The method of claim 3, further comprising providing identical sets of manually segmented test images and computer segmented images to multiple displays for receiving multiple scorings at the first computer in a blind randomized process.

5. The method of claim 1, wherein displaying on the test computer comprises displaying MR images having at least one of axial, sagittal, and coronal views with segmentations displayed as a respective translucent overlay thereon.

6. The method of claim 1, further comprising visually comparing a series of respective manually segmented test images and the computer segmented images with a display connected to the test computer, scoring the manually segmented test images and the computer segmented images and sending the score to the first computer over the network, wherein the scoring comprises selecting one numerical score from a scale including 0: No Match, 2: Very Poor Match, 4: Poor Match, 6: Good Match, 8: Very Good Match, 10: Perfect Match.

7. The system of claim 1, wherein scores for the accuracy of the manually segmented test images and the computer segmented images are entered into the test computer by a plurality of trained humans visually comparing the manually segmented test images and the computer segmented images on respective displays in a blind randomized process.

8. A computer implemented system of determining accuracy of a neural network in producing computerized segmentations within magnetic resonant (MR) images, comprising:
    a segmenting computer having a processor connected to computerized memory storing software implementing the neural network, the computerized memory storing adjustable settings for neural network configuration parameters, wherein the segmenting computer receives the MR images as inputs to the neural network and segments regions within the MR images with the neural network to produce computer segmented images;
    a first computer connected over the network to the segmenting computer, wherein the first computer saves the computer segmented images;
    using the first computer:
    communicating with test computers connected to the network, wherein the test computers display the computer segmented images alongside manually segmented test images for scoring; and
    receiving scores from the test computers for the accuracy of the manually segmented test images and the computer segmented images; and
    using the segmenting computer, updating the neural network configuration parameters after receiving the scores.

9. The system of claim 8, further comprising technician computers facilitating manual segmenting steps to produce the manually segmented images and storing the manually segmented images in the first computer connected to the network.

10. The system of claim 9, further comprising:
    scoring software saved in respective memory of the test computers, wherein the software retrieves the computer segmented images and the manually segmented images over the network;
    displays connected to the test computers for showing corresponding pairs of the manually segmented test images and the computer segmented images for scoring.

11. The system of claim 10, wherein the scoring software comprises a scoring application for entering scores for the manually segmented test images and the computer segmented test images.

12. The system of claim 11, wherein the scoring application is operates on a graphical user interface configured to display a scoring scale and a data entry mechanism.

13. The system of claim 11, wherein the scoring application is a slider scale displayed on the test computer and configured to enter into the test computer one numerical score from a scale including 0: No Match, 2: Very Poor Match, 4: Poor Match, 6: Good Match, 8: Very Good Match, 10: Perfect Match.

14. The system of claim 8, wherein the neural network configuration parameters comprise at least a number of training epochs and a learning rate step decay schedule.

15. The system of claim 8, wherein the segmenting computer comprises multiple instances of the neural network for image segmentation.

16. The system of claim 15, wherein the segmenting computer initializes each of the multiple instances of the neural network with respectively randomized weight parameters during a training phase of the neural network, prior to receiving the inputs of the MR images to be segmented.

17. The system of claim 8, wherein the MR images used as inputs to the neural network are pre-treatment images of a subject.

18. The system of claim 17, wherein the manually segmented test images were pre-processed to form a consensus segmentation from multiple segmentations of the same image.

19. The system of claim 8, wherein a training phase of utilizing the neural network comprises computing Dice coefficients of the manually segmented images and the computer segmented images.

* * * * *